United States Patent
Traneus

(10) Patent No.: US 12,350,521 B2
(45) Date of Patent: Jul. 8, 2025

(54) COMPUTER PROGRAM PRODUCT AND COMPUTER SYSTEM FOR PLANNING AND DELIVERING RADIOTHERAPY TREATMENT AND A METHOD OF PLANNING RADIOTHERAPY TREATMENT

(71) Applicant: RaySearch Laboratories AB, Stockholm (SE)

(72) Inventor: Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 335 days.

(21) Appl. No.: 17/627,222

(22) PCT Filed: Jul. 8, 2020

(86) PCT No.: PCT/EP2020/069223
§ 371 (c)(1),
(2) Date: Jan. 14, 2022

(87) PCT Pub. No.: WO2021/008962
PCT Pub. Date: Jan. 21, 2021

(65) Prior Publication Data
US 2022/0257981 A1 Aug. 18, 2022

(30) Foreign Application Priority Data
Jul. 15, 2019 (EP) .................................... 19186232

(51) Int. Cl.
*A61N 5/10* (2006.01)
(52) U.S. Cl.
CPC ......... *A61N 5/1064* (2013.01); *A61N 5/1031* (2013.01); *A61N 5/1042* (2013.01); *A61N 2005/1087* (2013.01)

(58) Field of Classification Search
None
See application file for complete search history.

(56) References Cited

U.S. PATENT DOCUMENTS

| | | | |
|---|---|---|---|
| 2010/0301228 A1 | 12/2010 | Pu | |
| 2011/0237859 A1* | 9/2011 | Kuhn | A61N 5/1031 600/1 |
| 2013/0259198 A1* | 10/2013 | Alezra | A61N 5/1042 378/65 |
| 2016/0175616 A1 | 6/2016 | Kwak et al. | |
| 2019/0022409 A1* | 1/2019 | Vanderstraten | A61N 5/1081 |
| 2020/0016431 A1* | 1/2020 | Swerdloff | G01R 33/10 |

FOREIGN PATENT DOCUMENTS

| | | |
|---|---|---|
| JP | 2006-341010 A | 12/2006 |
| JP | 2010-273785 A | 12/2010 |
| WO | WO-2012/070054 A1 | 5/2012 |

OTHER PUBLICATIONS

Indian Office Action issued Feb. 16, 2024 in Application No. 202117058130.

* cited by examiner

*Primary Examiner* — Marcus H Taningco
(74) *Attorney, Agent, or Firm* — Faegre Drinker Biddle & Reath LLP

(57) ABSTRACT

The trajectory of a beam of charged particles within a patient may be changed by the application of a magnetic field. In that way, the position of the beam's Bragg peak may be controlled for a beam having a specific direction and energy.

13 Claims, 2 Drawing Sheets

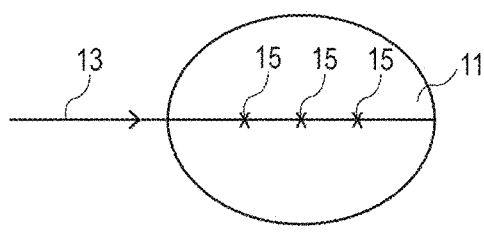
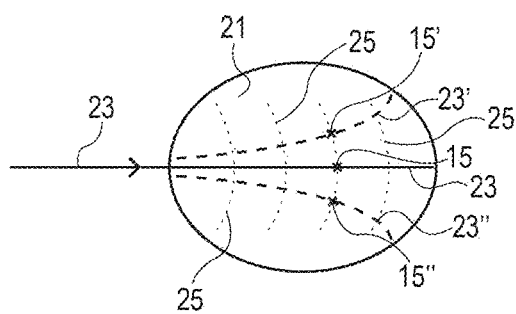
FIGURE 1  FIGURE 2
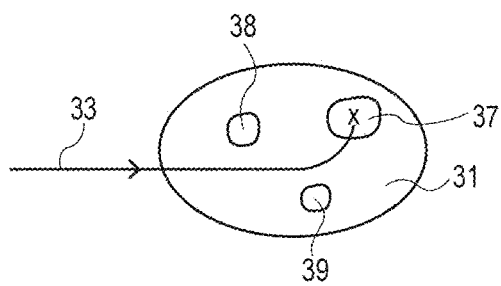
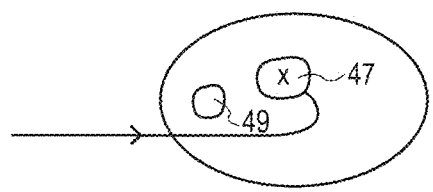
FIGURE 3  FIGURE 4
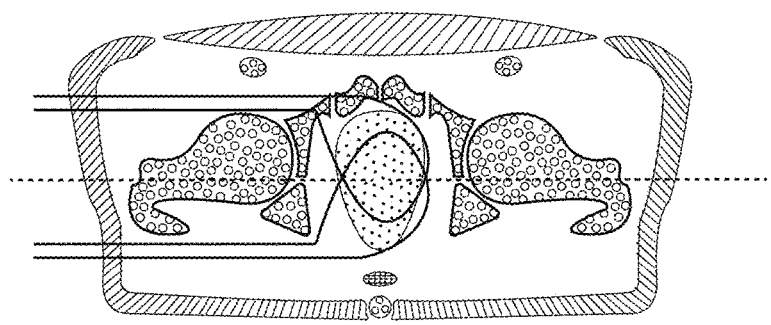
FIGURE 5

COMPUTER PROGRAM PRODUCT AND COMPUTER SYSTEM FOR PLANNING AND DELIVERING RADIOTHERAPY TREATMENT AND A METHOD OF PLANNING RADIOTHERAPY TREATMENT

CROSS REFERENCE TO RELATED APPLICATIONS

This application is a National Stage of International Application No. PCT/EP2020/069223, filed Jul. 8, 2020, and claims the benefit of European Patent Application No. 19186232.5, filed Jul. 15, 2019, the entire contents of each of which are incorporated herein by reference.

TECHNICAL FIELD

The present invention relates to a method, a computer program product and a computer system for radiotherapy treatment planning and to a system for delivery of radiotherapy treatment and a computer program product for controlling such delivery. More specifically, the invention relates to radiotherapy involving protons or other charged particles.

BACKGROUND

In radiotherapy treatment, the use of protons or other charged particles has several advantages. In particular, a proton will depose most of its energy towards the end of its path, in the so-called Bragg peak, so that the dose can be deposited within a target in the patient with great accuracy. The position of the Bragg peak depends on the energy of the protons and the density of the tissues they traverse. To cover a target area such as a tumor, protons having different energy levels are applied, so that their Bragg peaks will be distributed over the tumor.

A common challenge in radiotherapy treatment planning is ensuring a sufficiently high dose to the target, while limiting the dose to the surrounding tissue so that in particular organs at risk are not damaged. In some cases, depending on patient geometry, this can be difficult, when organs at risk are located close to the target, or even in the path from the radiation source to the target.

SUMMARY

It is an object of the present invention to increase the efficiency, precision and flexibility of radiotherapy treatment using protons or other charged particles.

This object is achieved according to the present invention by a computer-implemented method of producing a radiotherapy treatment plan for treatment of a patient with at least one treatment field, comprising at least one beam of charged particles, such as protons, in which each beam will deposit energy in a Bragg peak, including the steps, for each beam, of
  determining a desired position of the Bragg peak for the beam, typically within a target
  determining a desired path for the beam to reach the determined desired position,
  determining an energy level and direction for the beam and a set of properties of a first magnetic field to be applied to the beam within the patient to control the direction of the beam to ensure that the beam will follow the desired path and that its Bragg peak will be placed in the determined desired position.

According to the invention, a proton-based radiotherapy plan can be tailored by affecting the trajectory of the protons, or other charged particles, by the application of a magnetic field, preferably a variable magnetic field. In this way, the direction of the protons inside the patient may be affected so that the Bragg peak is not necessarily located along a straight line from the radiation source through the entry point on the patient. Instead, the particle can be made to follow a suitable path to cause the Bragg peak to be positioned in the desired place. In a preferred embodiment, one point of entry of the beam is used. This will give a high dose in one entry point but also enables all surrounding tissue to be spared.

The actual path of each beam can be controlled by its energy and direction, and the properties of the magnetic field. The beams will have the highest energy when entering the patient, and will lose energy as they pass through the patient. Since the magnetic field will affect particles having a lower energy more than particles having a high energy, the beam will be bent more closer to the Bragg peaks, which should be placed in the target volume. Because of this, the beams can, for example, be made to pass directly through some tissue and then change direction. The set of properties of the magnetic field includes a strength and direction and optionally a spatial variation of the magnetic field.

In some embodiments, the set of properties of the magnetic field is determined before the energy level and direction of the beam and the energy level and direction of the beam are determined in dependence of the properties of the magnetic field. Alternatively, the energy level and direction of the beam may be determined before the properties of the magnetic field and the properties of the magnetic field are determined in dependence of the energy level and direction of the beam. The best results may be obtained if the properties of the magnetic field and the energy level and direction of the beam are determined iteratively by joint optimization.

The energy level and direction of the beam, and the properties of the magnetic field, may be used in the generation of the radiotherapy treatment plan.

The invention also relates to a computer program product for producing a radiotherapy treatment plan, which when performed in a computer, will cause the computer to perform the method according to any one of the preceding claims. The computer program product may be stored on a memory device, such as a non-transitory memory device. The invention also relates to a computer system comprising a processor and a program memory, the program memory comprising a computer program product as defined above.

Aspects of the invention also relate to the delivery of radiotherapy treatment to a patient. Therefore, the invention also relates to a computer program product for controlling the delivery of radiotherapy treatment from a delivery apparatus to a patient, said treatment involving radiating the patient with at least one beam of charged particles such as protons, comprising computer-readable code means which when run in a processor of an apparatus for providing radiotherapy treatment will cause the apparatus to radiate the patient with the at least one beam while applying a first magnetic field arranged to bend the paths of the particles, thereby controlling the position of the particle's Bragg peaks within the patient. As discussed above, the properties of the magnetic field include strength and direction and possibly temporal and/or spatial variation of the field.

The method may further comprise applying a second magnetic field, different from the first magnetic field, to bend the paths of other particles to place their Bragg peaks in a different position.

The invention also relates to an apparatus for providing radiotherapy treatment to a patient, said apparatus comprising a radiation source arranged to emit a beam comprising charged particles such as protons, and means for shaping said beam, the apparatus further comprising a device arranged to generate a magnetic field for modifying the path of at least one particle within the patient, and preferably processing means arranged to control the device in such a way as to modify the magnetic field. The device may be arranged to generate a magnetic field that will bend the path of the particles near their Bragg peaks. The device may also be arranged to vary the magnitude and/or direction of the magnetic field with time.

Magnetic fields are commonly used in the field of radiotherapy for shaping and directing beams before they are emitted towards the patient. The invention proposes to use magnetic fields to direct beams within the patient.

BRIEF DESCRIPTION OF THE DRAWINGS

The invention will be described in more detail in the following, by way of example and with reference to the appended drawings, in which FIG. 1 shows, schematically, a beam passing through a patient.

FIG. 2 shows, schematically, possible trajectories of the beam that may be achieved according to the invention.

FIGS. 3 and 4 illustrate possible proton paths according to embodiments of the invention FIG. 5 illustrates an example of providing radiation to a prostate

DETAILED DESCRIPTION

Figure 6:
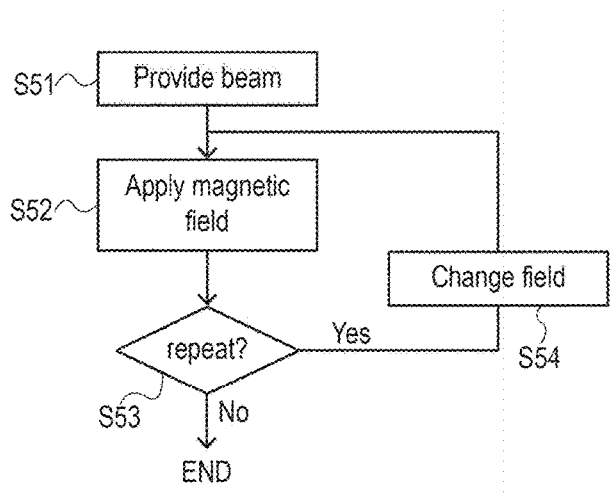
FIG. 6 is a flow chart of a treatment method according to the invention

FIG. 1 shows, schematically, a section through a patient 11, and a beam 13 comprising charged particles such as protons, passing through the patient along a substantially straight line, until it stops and deposits most of its energy in the Bragg peak. As is well known in the art, the path length of the beam inside the patient and thereby the position of the Bragg peak, can be controlled by controlling the energy of the particles, in dependence of patient geometry, in particular the densities of the tissues the particles will traverse. This is indicated in FIG. 1 by marking three possible points for the Bragg peaks 15 along the path with an x. The positions may be chosen as desired in dependence of the target's position.

FIG. 2 shows the same schematic section through a patient 21 and the same beam 23 as in FIG. 1, shown as a solid line. FIG. 2 also shows a first and a second alternative path 23', 23" that may be taken by the particles if a first or a second magnetic field is applied to the beam. As before, the path length will depend on the energy of the particle, and to some extent on the patient geometry as mentioned above. Points on the different paths corresponding to the same path length are indicated by means of arcs 25 shown as dashed lines. The deviation of the particle's trajectory from the solid straight line 23 may be determined by controlling the strength and other properties of the magnetic field. Typically, the magnetic field is non-homogeneous. In preferred embodiments the direction of the magnetic field can also be varied, to enable variation of the path in three dimensions. As can be seen in FIG. 2 the alternative paths 23', 23" bend gradually more and more along the path, since the particles will be affected more by the magnetic field as they lose energy along the path. Three alternative Bragg peak positions 15, 15' and 15" are indicated corresponding to the same path length for the three different trajectories 23, 23', 23".

FIG. 3 shows schematically a situation in which the method according to the invention can be used. Again, a section through a patient 31 is shown, including a target 37 that is to receive at least a minimum dose and a first 38 and a second 39 organ at risk that should receive as little dose as possible. With conventional treatment this would be a problem because there is no straight path from the radiation source to the target 37 without passing through an organ at risk. According to the present invention, a magnetic field can be applied which, in combination with the particle's initial energy and direction, will cause the incoming particles to follow a particular trajectory through the patient that will avoid both of the organs at risk 38, 39 and place their Bragg peaks in the target 37. One such trajectory is shown in FIG. 3.

FIG. 4 shows a situation in which the beam trajectory can be changed even more, by applying a stronger magnetic field. In this case, the beam 43 is caused to bend more than in FIG. 3, enabling the proton beam to take a path past the organ at risk 49 and around it so that the Bragg peak, marked by x, will be placed in the target 47. Of course, different fields may be applied for different beams during the treatment to enable the whole target to be covered by Bragg peaks.

Another situation in which the methods according to the invention will be advantageous is where a tumor has an irregular shape and therefore is difficult to cover with conventional therapy methods without affecting surrounding tissue.

FIG. 5 illustrates a more realistic, albeit somewhat idealized, example of a situation in which the inventive method may be particularly useful. A section through a patient is shown, including the patient's prostate and hip bones. Normally, radiotherapy to the prostate is effected from two opposite directions, through the hip bones, as illustrated by a dashed lines through the hip bone. This is done to avoid damaging other sensitive tissue such as the rectum and the urine bladder but often leads to problems with the hip joint several years after the radiotherapy treatment. According to the invention, the radiotherapy could be performed from one or preferably two entry points on either side of the hip joint. The beam enters beside the hip joint, in parallel with the femoral neck, and is bent by a magnetic field to reach the prostate. As can be seen, for good coverage of the prostate preferably two beams are used as explained above. It would also be possible to use two beams from opposite sides of the patient, or to use three or more beams.

FIG. 6 is a flow chart of a treatment method according to the invention, indicating one possible sequence of steps. As will be understood, the order in which each magnetic field and no magnetic field is applied may be varied as suitable. In a first step S51 a beam of charged particles is applied. In a second step S52, a magnetic field is generated which will cause the beam path to deviate from a straight line. Step S53 is a decision step to see if the magnetic field should be changed before continuing the treatment. If yes, the procedure continues with a step S54 in which the magnetic field settings are changed and returns to step S52. The decision is typically made according a treatment plan. If no, the procedure stops.

Figure 7:
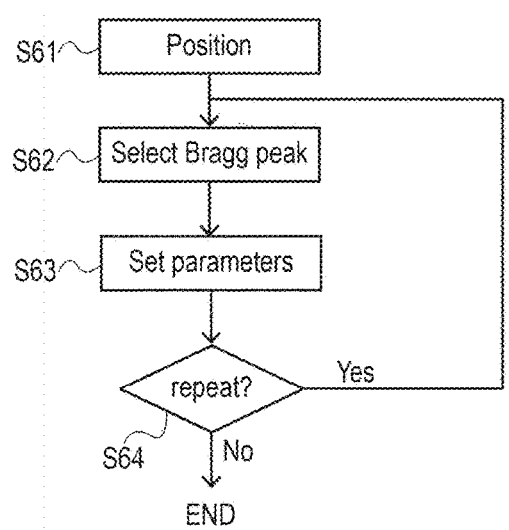
FIG. 7 is a flow chart of a treatment planning method according to the invention

FIG. 7 is a flow chart of a treatment planning method according to the invention. In a first step S61, the position of a target is determined and the desired positions of one or more Bragg peaks within the target are determined. Ideally, the Bragg peaks should be positioned in such a way that they secure a uniform dose to the whole target. In a second step S62, one of the desired Bragg peak positions is selected and a possible path through the patient to the selected Bragg peak position is determined. In a third step S63, the particle energy needed to reach the selected Bragg peak position, and the magnitude and direction of the magnetic field that will cause the particle to reach the selected Bragg peak position is determined. As discussed above, the combination of particle energy, the particle's initial direction, and the properties of the magnetic field should cause the particle to follow a path that will avoid any organs at risk while depositing the main part of its energy at the selected Bragg peak position. Step S64 is a decision step in which it is decided whether the planning steps should be repeated for another Bragg peak position. If yes, the procedure returns to step S62 for selection of a new Bragg peak position; if no, the procedure ends.

The magnetic field is characterized by a set of properties including at least its strength and direction. Typically, the magnetic field will be non-homogeneous. In that case the set of properties also includes information about the spatial variation of the magnetic field, typically in the form of a 3D vector field. The magnetic field may also be arranged to vary with time.

Figure 8:
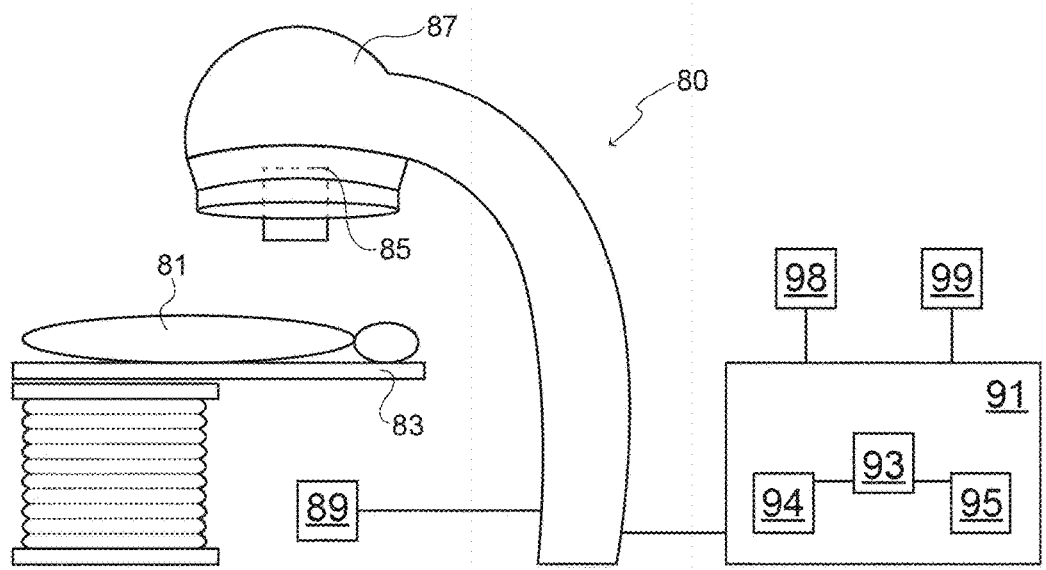
FIG. 8 shows an example of a general dose delivery system that may also be used for treatment planning

FIG. 8 is a schematic overview of a system 80 for radiotherapy treatment and/or treatment planning. As will be understood, such systems may be designed in any suitable way and the design shown in FIG. 8 is only an example. A patient 81 is positioned on a treatment couch 83. The system comprises an imaging/treatment unit having a radiation source 85 mounted in a gantry 87 for emitting radiation towards the patient positioned on the couch 83. Typically, the couch 83 and the gantry 87 are movable in several dimensions relative to each other, to provide radiation to the patient as flexibly and correctly as possible. These parts and their functions are well known to the skilled person. A number of devices provided to shape the beam laterally and in depth are typically present and will be not be discussed in more detail here. In this example the system also comprises means 89 for generating a magnetic field that will affect the path of the particles of the beam inside the patient's body and means for modifying the magnetic field. The means 89 for generating the magnetic field may be any suitable means, such as one or more magnets, or one or more coils. The modifying means can be any type of means, for example arranged to modify the position and direction of the magnets or coils, and to control the current through the coils. The system also comprises a computer 91 which may be used for radiotherapy treatment planning and/or for controlling radiotherapy treatment. As will be understood, the computer 91 may be a separate unit not connected to the imaging/treatment unit.

The computer 91 comprises a processor 93, a data memory 94, and a program memory 95. Preferably, one or more user input means 98, 99 are also present, in the form of a keyboard, a mouse, a joystick, voice recognition means or any other available user input means. The user input means may also be arranged to receive data from an external memory unit.

When the system is used for planning, the data memory 94 comprises clinical data and/or other information used to obtain a treatment plan. Typically, the data memory 94 comprises one or more patient images to be used in treatment planning Field maps depicting possible magnetic fields must be available, for example, in the data memory 94. The field maps are input to the particle transport simulation being part of the dose computation. The program memory 95 holds at least one computer program arranged to cause the processor to perform a treatment planning method according to FIG. 7. The program memory 95 also holds a computer program arranged to make the computer perform the method steps discussed in connection with FIG. 6 to make the computer control the radiotherapy treatment of a patient. The program memory 95 may also hold a computer program arranged to control the magnetic field, for example, by controlling a current, and/or the position of the magnetic field generating means 89.

As will be understood, the data memory 94 and the program memory 95 are shown and discussed only schematically. There may be several data memory units, each holding one or more different types of data, or one data memory holding all data in a suitably structured way, and the same holds for the program memories. One or more memories may also be stored on other computers. For example, the computer may be arranged to perform only one of the methods, there being another computer for performing the optimization.

The invention claimed is:

1. A computer-implemented method of producing a radiotherapy treatment plan for treatment of a patient with at least one treatment field, comprising at least one beam of charged particles, in which each beam will deposit energy in a Bragg peak, the method comprising, for each beam:
   determining a desired position of the Bragg peak for the beam within a target;
   determining a desired path for the beam to reach the determined desired position; and
   determining an energy level and direction for the beam and a set of properties of a first variable magnetic field to be applied to the beam within the patient to control the direction of the beam to ensure that the beam will follow the desired path and that the Bragg peak of the beam will be placed in the determined desired position, the direction of the beam is controlled to deviate from a straight line path to the desired path,
   wherein the beam of charged particles is applied before the first variable magnetic field is generated,
   wherein the first variable magnetic field is generated to control the direction of the beam to deviate from the straight line path to the desired path,
   wherein after the first variable magnetic field is generated, changing the set of properties of the first variable magnetic field to a set of proprieties of a second variable magnetic field,
   wherein after the first variable magnetic field is generated, the second variable magnetic field is generated to control the direction of the beam to the desired path, and
   wherein the properties of the first variable magnetic field, the properties of the second variable magnetic field, and the energy level and direction of the beam are determined iteratively by joint optimization.

2. The method according to claim 1, wherein the set of properties of the first variable magnetic field includes a strength and direction and a spatial variation of the first variable magnetic field.

3. The method according to claim 1, wherein the set of properties of the first variable magnetic field is determined before the energy level and direction of the beam and the energy level and direction of the beam are determined in dependence of the properties of the first variable magnetic field.

4. The method according to claim 1, wherein the energy level and direction of the beam are determined before the properties of the first variable magnetic field and the properties of the first variable magnetic field are determined in dependence of the energy level and direction of the beam.

5. The method according to claim 1, further comprising generating the radiotherapy treatment plan including the energy level, direction, and set of properties.

6. A computer program product for producing a radiotherapy treatment plan, which when performed in a computer, will cause the computer to perform the method according to claim 1.

7. A computer system comprising a processor and a program memory, the program memory comprising the computer program product according to claim 6.

8. A computer program product for controlling the delivery of radiotherapy treatment from a delivery apparatus to a patient, said treatment involving radiating the patient with at least one beam of charged particles, in which each beam will deposit energy in a Bragg peak, comprising non-transitory computer-readable code which when run in a processor of an apparatus for providing radiotherapy treatment will cause the apparatus to perform the following:
radiating the patient with the at least one beam while applying a first variable magnetic field arranged to bend the paths of the particles, thereby controlling the position of the particle's Bragg peaks within the patient, the first variable magnetic field is generated to deviate from a straight line path,
wherein after the first variable magnetic field is applied, changing a set of properties of the first variable magnetic field to a set of proprieties of a second variable magnetic field,
wherein after the first variable magnetic field is generated, the second variable magnetic field is applied to control the direction of the beam from the straight line path to a desired path,
wherein properties of the first variable magnetic field, the properties of the second variable magnetic field, and an energy level and direction of the at least one beam are determined iteratively by joint optimization.

9. The computer program product according to claim 8, wherein the second variable magnetic field is different from the first variable magnetic field bends the paths of other particles to place their Bragg peaks in a different position.

10. An apparatus for providing radiotherapy treatment to a patient, said apparatus comprising a radiation source arranged to emit a beam comprising charged particles, in which each beam will deposit energy in a Bragg peak, and a beam shaper that shapes said beam, the apparatus further comprising a device arranged to generate a first variable magnetic field for modifying the path of at least one particle within the patient, the first variable magnetic field is controlled to deviate from a straight line path, thereby controlling the position of the particle's Bragg peak within the patient,
wherein the beam of charged particles is applied before the first variable magnetic field is generated,
wherein the first variable magnetic field is generated to control the direction of the beam to deviate from the straight line path to the desired path,
wherein after the first variable magnetic field is generated, changing the set of properties of the first variable magnetic field to a set of proprieties of a second variable magnetic field,
wherein after the first variable magnetic field is generated, the second variable magnetic field is generated to control the direction of the beam to the desired path, and
wherein properties of the first variable magnetic field, the properties of the second variable magnetic field, and an energy level and direction of each beam are determined iteratively by joint optimization.

11. The apparatus according to claim 10, further comprising at least one processor arranged to control the device in such a way as to modify the first variable magnetic field.

12. The apparatus according to claim 10, wherein the device is arranged to generate the first variable magnetic field that will bend the path of the particles near their Bragg peaks.

13. The apparatus according to claim 10, wherein the device is arranged to vary the magnitude and/or direction of the first variable magnetic field with time.

* * * * *